(12) United States Patent
Hassan et al.

(10) Patent No.: US 8,168,836 B2
(45) Date of Patent: *May 1, 2012

(54) METHOD OF HYDROGENATING ALDEHYDES AND KETONES

(75) Inventors: Abbas Hassan, Sugar Land, TX (US); Ebrahim Bagherzadeh, Sugar Land, TX (US); Rayford G. Anthony, College Station, TX (US); Gregory Borsinger, Chatham, NJ (US); Azziz Hassan, Sugar Land, TX (US)

(73) Assignee: H R D Corporation, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/031,977

(22) Filed: Feb. 22, 2011

(65) Prior Publication Data

US 2011/0201849 A1 Aug. 18, 2011

Related U.S. Application Data

(60) Continuation of application No. 12/335,253, filed on Dec. 15, 2008, now Pat. No. 7,914,746, which is a division of application No. 12/142,419, filed on Jun. 19, 2008, now Pat. No. 7,479,576.

(60) Provisional application No. 60/946,478, filed on Jun. 27, 2007.

(51) Int. Cl.
*C07C 29/141* (2006.01)
*C07C 29/145* (2006.01)

(52) U.S. Cl. ..................................... 568/881

(58) Field of Classification Search .................. 568/881
See application file for complete search history.

(56) References Cited

U.S. PATENT DOCUMENTS

| | | |
|---|---|---|
| 2,520,424 A | 8/1950 | Victor et el. |
| 3,781,320 A | 12/1973 | Irwin |
| 3,869,518 A | 3/1975 | Sze et al. |
| 3,996,012 A | 12/1976 | Zucker |
| 4,072,720 A | 2/1978 | Haag et al. |
| 4,418,227 A | 11/1983 | Pez et al. |
| 4,724,269 A | 2/1988 | Suzuki et al. |
| 4,886,905 A | 12/1989 | Larkins, Jr. |
| 4,914,029 A | 4/1990 | Caransa et al. |
| 4,950,831 A | 8/1990 | Staton et al. |
| 5,004,845 A | 4/1991 | Bradley et al. |
| 5,009,816 A | 4/1991 | Weise et al. |
| 5,264,087 A | 11/1993 | Lowery et al. |
| 5,382,358 A | 1/1995 | Yeh |
| 5,451,348 A | 9/1995 | Kingsley |
| 5,506,363 A | 4/1996 | Grate et al. |
| 5,679,870 A | 10/1997 | Tustin et al. |
| 5,710,342 A | 1/1998 | Imre et al. |
| 5,710,355 A | 1/1998 | Krishnamurti |
| 5,756,714 A | 5/1998 | Antrim et al. |
| 5,877,350 A | 3/1999 | Langer et al. |
| 6,194,625 B1 | 2/2001 | Graves et al. |
| 6,241,472 B1 | 6/2001 | Bosch et al. |
| 6,251,289 B1 | 6/2001 | Sherman |
| 6,331,314 B1 | 12/2001 | Klinksiek et al. |
| 6,368,366 B1 | 4/2002 | Langer et al. |
| 6,368,367 B1 | 4/2002 | Langer et al. |
| 6,383,237 B1 | 5/2002 | Langer et al. |
| 6,441,255 B1 | 8/2002 | Haas et al. |
| 6,693,213 B1 | 2/2004 | Kolena et al. |
| 6,768,021 B2 | 7/2004 | Horan et al. |
| 6,787,036 B2 | 9/2004 | Long |
| 6,809,217 B1 | 10/2004 | Colley et al. |
| 6,866,411 B1 | 3/2005 | Stelzer et al. |
| 7,461,970 B2 | 12/2008 | Brown |
| 2003/0114720 A1 | 6/2003 | Hoffmann et al. |
| 2004/0052158 A1 | 3/2004 | Holl |
| 2006/0272634 A1 | 12/2006 | Nehmer et al. |
| 2007/0030322 A1 | 2/2007 | Lee et al. |
| 2009/0136392 A1 | 5/2009 | Hassan et al. |
| 2009/0136393 A1 | 5/2009 | Hassan et al. |
| 2009/0136396 A1 | 5/2009 | Hassan et al. |
| 2009/0323458 A1 | 12/2009 | Fischer et al. |

FOREIGN PATENT DOCUMENTS

| | | |
|---|---|---|
| EP | 1604969 A | 12/2005 |
| GB | 2175896 A | 12/1986 |
| GB | 2269116 A | 2/1994 |
| JP | 61183235 A | 8/1986 |
| JP | 2000143706 A | 5/2000 |
| JP | 2002003505 A | 1/2002 |
| JP | 2002121353 A | 4/2002 |
| JP | 2007505201 A | 3/2007 |
| WO | 9843725 A | 10/1998 |
| WO | 2004050591 A1 | 6/2004 |
| WO | 2005108533 A2 | 11/2005 |
| WO | 2007023864 Y | 3/2007 |

OTHER PUBLICATIONS

Office Action Dated Apr. 20, 2010 for U.S. Appl. No. 12/411,660.
Office Action Dated Apr. 20, 2010 for U.S. Appl. No. 12/427,286.
Office Action Dated Apr. 23, 2010 for U.S. Appl. No. 12/568,155.
Office Action Dated Apr. 27, 2010 for U.S. Appl. No. 12/568,280.
Office Action Dated May 5, 2010 for U.S. Appl. No. 12/142,120.
Office Action Dated Jun. 25, 2009 for U.S. Appl. No. 12/142,447.
Office Action Dated Jan. 7, 2010 for U.S. Appl. No. 12/142,447.
Office Action Dated May 13, 2010 for U.S. Appl. No. 12/142,447.
Office Action Dated Feb. 4, 2010 for U.S. Appl. No. 12/492,721.
Office Action Dated Feb. 18, 2010 for U.S. Appl. No. 12/635,433.
Office Action Dated Feb. 18, 2010 for U.S. Appl. No. 12/635,454.
Office Action Dated May 14, 2010 for U.S. Appl. No. 12/137,441.
Office Action Dated Feb. 19, 2010 for U.S. Appl. No. 12/144,459.
Office Action Dated Sep. 2, 2009 for U.S. Appl. No. 12/142,433.
Office Action Dated Jan. 29, 2010 for U.S. Appl. No. 12/142,433.
Office Action Dated May 24, 2010 for U.S. Appl. No. 12/142,433.
Office Action Dated Apr. 30, 2010 for U.S. Appl. No. 12/141,191.
Office Action Dated Oct. 27, 2009 for U.S. Appl. No. 12/142,120.

(Continued)

*Primary Examiner* — Elvis O Price

(74) *Attorney, Agent, or Firm* — Timothy S. Westby; Porter Hedges LLP

(57) ABSTRACT

Methods and systems for the hydrogenation of aldehydes and/or ketones are described herein. The methods and systems incorporate the novel use of a high shear device to promote dispersion and solubility of the hydrogen-containing gas (e.g. $H_2$ gas) in the aldehydes and/or ketones. The high shear device may allow for lower reaction temperatures and pressures and may also reduce hydrogenation time with existing catalysts.

20 Claims, 2 Drawing Sheets

OTHER PUBLICATIONS

Office Action Dated May 5, 2010 for U.S. Appl. No. 12/571,537.
Office Action Dated Jul. 28, 2010 for U.S. Appl. No. 12/635,433.
Office Action Dated Jun. 28, 2010 for U.S. Appl. No. 12/335,253.
Office Action Dated Jun. 28, 2010 for U.S. Appl. No. 12/335,272.
International Application No. PCT/US2008/066572 International Search Report dated Aug. 28, 2008, 3 pages.
International Application No. PCT/US2008/068207 International Search Report dated Oct. 14, 2008, 5 pages.
International Application No. PCT/US2008/068161 International Search Report dated Sep. 24, 2008, 7 pages.
European Search Report dated Mar. 29, 2011 for corresponding European Application No. 08771646.4 (5 pgs.).

METHOD OF HYDROGENATING ALDEHYDES AND KETONES

CROSS-REFERENCE TO RELATED APPLICATIONS

This application is a continuation application of U.S. patent application Ser. No. 12/335,253, filed Dec. 15, 2008, which is a divisional application of U.S. patent application Ser. No. 12/142,419, filed Jun. 19, 2008, which claims the benefit under 35 U.S.C. §119(e) of U.S. Provisional Patent Application No. 60/946,478, filed Jun. 27, 2007. The disclosure of said applications is hereby incorporated herein by reference.

STATEMENT REGARDING FEDERALLY SPONSORED RESEARCH OR DEVELOPMENT

Not Applicable.

TECHNICAL FIELD

The invention generally relates to apparatus and methods for hydrogenating aldehydes and/or ketones, and more particularly related to the acceleration of such reactions by high shear mixing.

BACKGROUND OF THE INVENTION

Aldehydes, ketones and corresponding primary alcohols are general classes of organic compounds. There are several methods known in any textbook of organic chemistry and in patent literature for the conversion of aldehydes to the corresponding primary alcohols, such as chemical reduction methods using alkali or alkaline earth metal-derived borohydrides or aluminium hydrides and metal catalyzed-hydrogenation. Thus, the conversion of aldehydes and ketones into the corresponding alcohols by catalytic hydrogenation is well known. As such, efforts to optimize aldehyde and/or ketone hydrogenation have been focused on catalyst technology. Nickel carrier catalysts or Raney nickel are frequently used as catalysts for the hydrogenation of aldehydes and ketones. The catalyst simultaneously binds the $H_2$ and the aldehyde and/or ketone and facilitates their union. Platinum group metals, particularly platinum, palladium, rhodium and ruthenium, are examples of highly active catalysts. Highly active catalysts operate at lower temperatures and lower pressures of $H_2$. Non-precious metal catalysts, especially those based on nickel (such as Raney nickel and Urushibara nickel) have also been developed as economical alternatives but they are often slower or require higher temperatures. The trade-off is activity (speed of reaction) vs. cost of the catalyst and cost of the apparatus required for use of high pressures.

Little attention has been paid with regard to non-chemical methods to accelerate the hydrogenation of aldehydes and/or ketones. Consequently, there is a need for alternative methods for accelerating the hydrogenation of aldehydes and/or ketones for the production of alcohol.

SUMMARY

Methods and systems for the hydrogenation of aldehydes and/or ketones are described herein. The methods and systems incorporate the novel use of a high shear device to promote dispersion and solubility of the hydrogen-containing gas (e.g. $H_2$ gas) in the aldehydes and/or ketones. The high shear device may allow for lower reaction temperatures and pressures and may also reduce hydrogenation time with existing catalysts. Further advantages and aspects of the disclosed methods and system are described below.

In an embodiment, a method of hydrogenating an aldehyde or a ketone comprises introducing a hydrogen-containing gas into an aldehyde or ketone stream to form a gas-liquid stream. The method further comprises flowing the gas-liquid stream through a high shear device so as to form a dispersion with gas bubbles having a mean diameter less than about 1 micron. In addition the method comprises contacting the gas-liquid stream with a catalyst in a reactor to hydrogenate the aldehyde or the ketone.

In an embodiment, a system for the hydrogenation of an aldehyde or a ketone comprises at least one high shear device configured for hydrogenating an aldehyde, a ketone, or combinations thereof The high shear device comprises a rotor and a stator. The rotor and the stator are separated by a shear gap in the range of from about 0.02 mm to about 5 mm. The shear gap is a minimum distance between the rotor and the stator. The high shear device is capable of producing a tip speed of the at least one rotor of greater than about 23 m/s (4,500 ft/min). In addition, the system comprises a pump configured for delivering a liquid stream comprising liquid phase to the high shear device.

The foregoing has outlined rather broadly the features and technical advantages of the present invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

DETAILED DESCRIPTION

The disclosed methods and systems for the hydrogenation of aldehydes and/or ketones employ a high shear mechanical device to provide rapid contact and mixing of the hydrogen-containing gas and aldehydes and/or ketones in a controlled environment in the reactor/mixer device. The term "hydrogen-containing gas" as used herein includes both substantially pure hydrogen gas as well as gaseous mixtures containing hydrogen. In particular, embodiments of the systems and methods may be used in the production of alcohols from the hydrogenation of aldehydes and/or ketones. Preferably, the method comprises a heterogeneous phase reaction of liquid aldehydes and/or ketones with a hydrogen-containing gas. The high shear device reduces the mass transfer limitations on the reaction and thus increases the overall reaction rate.

Chemical reactions involving liquids, gases and solids rely on time, temperature, and pressure to define the rate of reactions. In cases where it is desirable to react two or more raw materials of different phases (e.g. solid and liquid; liquid and gas; solid, liquid and gas), one of the limiting factors in controlling the rate of reaction involves the contact time of the reactants. In the case of heterogeneously catalyzed reactions there is the additional rate limiting factor of having the reacted products removed from the surface of the catalyst to enable the catalyst to catalyze further reactants. Contact time for the reactants and/or catalyst is often controlled by mixing which provides contact with two or more reactants involved in a chemical reaction. A reactor assembly that comprises an external high shear device or mixer as described herein makes possible decreased mass transfer limitations and thereby allows the reaction to more closely approach kinetic limitations. When reaction rates are accelerated, residence times may be decreased, thereby increasing obtainable throughput. Product yield may be increased as a result of the high shear system and process. Alternatively, if the product yield of an existing process is acceptable, decreasing the required residence time by incorporation of suitable high shear may allow for the use of lower temperatures and/or pressures than conventional processes.

Figure 1:
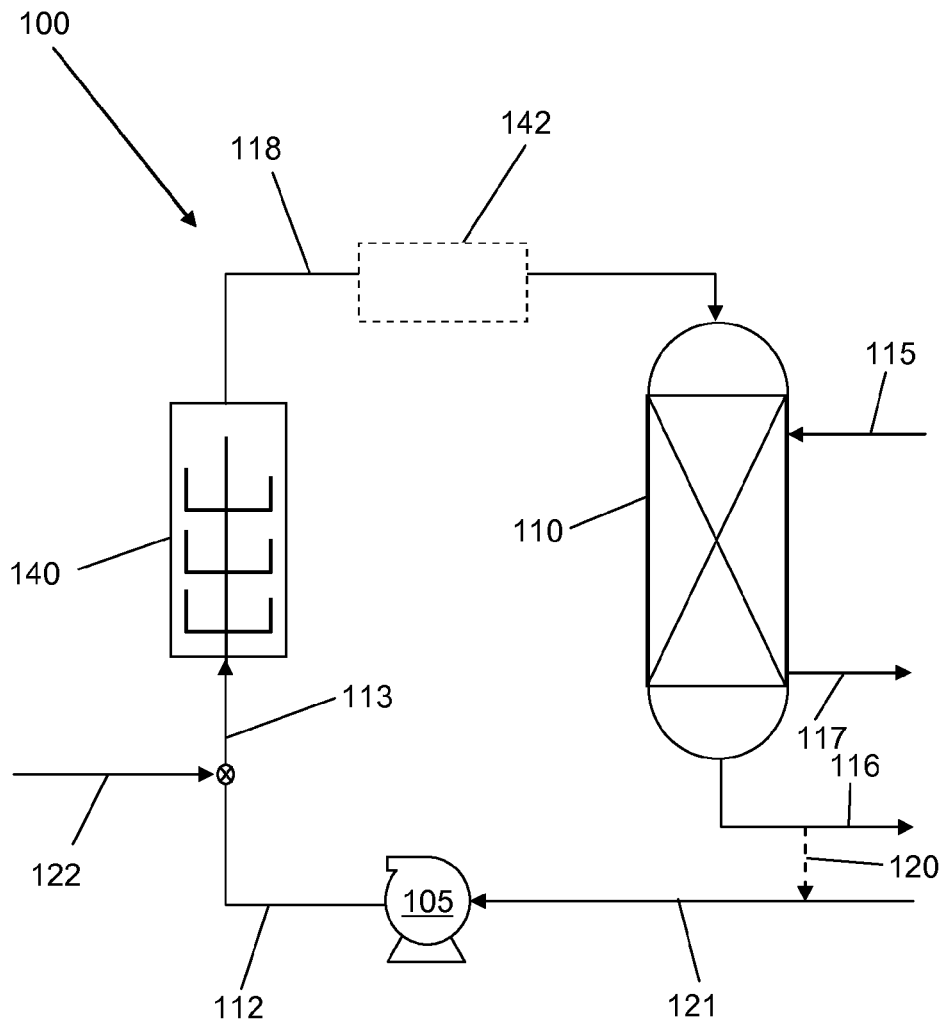
FIG. 1 is a process flow diagram of a process for the hydrogenation of an aldehyde or a ketone, according to certain embodiments of the invention.

System for Hydrogenation of Aldehydes and Ketones. A high shear aldehyde and/or ketone hydrogenation system will now be described in relation to FIG. 1, which is a process flow diagram of an embodiment of a high shear system 100 for the production of alcohols via the hydrogenation of aldehydes and/or ketones. The basic components of a representative system include external high shear device (HSD) 140, vessel 110, and pump 105. As shown in FIG. 1, the high shear device may be located external to vessel/reactor 110. Each of these components is further described in more detail below. Line 121 is connected to pump 105 for introducing either an aldehyde and/or ketone reactant. Line 113 connects pump 105 to HSD 140, and line 118 connects HSD 140 to vessel 110. Line 122 is connected to line 13 for introducing an hydrogen-containing gas. Line 117 is connected to vessel 110 for removal of unreacted aldehydes and/or ketones, and other reaction gases. Additional components or process steps may be incorporated between vessel 110 and HSD 140, or ahead of pump 105 or HSD 140, if desired. High shear devices (HSD) such as a high shear device, or high shear mill, are generally divided into classes based upon their ability to mix fluids. Mixing is the process of reducing the size of inhomogeneous species or particles within the fluid. One metric for the degree or thoroughness of mixing is the energy density per unit volume that the mixing device generates to disrupt the fluid particles. The classes are distinguished based on delivered energy density. There are three classes of industrial mixers having sufficient energy density to consistently produce mixtures or emulsions with particle or bubble sizes in the range of 0 to 50 microns. High shear mechanical devices include homogenizers as well as colloid mills.

Homogenization valve systems are typically classified as high energy devices. Fluid to be processed is pumped under very high pressure through a narrow-gap valve into a lower pressure environment. The pressure gradients across the valve and the resulting turbulence and cavitations act to break-up any particles in the fluid. These valve systems are most commonly used in milk homogenization and can yield average particle size range from about 0.01 µm to about 1 µm. At the other end of the spectrum are high shear device systems classified as low energy devices. These systems usually have paddles or fluid rotors that turn at high speed in a reservoir of fluid to be processed, which in many of the more common applications is a food product. These systems are usually used when average particle, or bubble, sizes of greater than 20 microns are acceptable in the processed fluid.

Between low energy—high shear devices and homogenization valve systems, in terms of the mixing energy density delivered to the fluid, are colloid mills, which are classified as intermediate energy devices. The typical colloid mill configuration includes a conical or disk rotor that is separated from a complementary, liquid-cooled stator by a closely-controlled rotor-stator gap, which is maybe between 0.025 mm and 10.0 mm. Rotors are usually driven by an electric motor through a direct drive or belt mechanism. Many colloid mills, with proper adjustment, can achieve average particle, or bubble, sizes of about 0.01 µm to about 25 µm in the processed fluid. These capabilities render colloid mills appropriate for a variety of applications including colloid and oil/water-based emulsion processing such as that required for cosmetics, mayonnaise, silicone/silver amalgam formation, or roofing-tar mixing.

An approximation of energy input into the fluid (kW/L/min) can be made by measuring the motor energy (kW) and fluid output (L/min). In embodiments, the energy expenditure of a high shear device is greater than 1000 W/m$^3$. In embodiments, the energy expenditure is in the range of from about 3000 W/m$^3$ to about 7500 W/m$^3$. The shear rate generated in a high shear device may be greater than 20,000 s$^{-1}$. In embodiments, the shear rate generated is in the range of from 20,000 s$^{-1}$ to 100,000 s$^{-1}$.

Tip speed is the velocity (m/sec) associated with the end of one or more revolving elements that is transmitting energy to the reactants. Tip speed, for a rotating element, is the circumferential distance traveled by the tip of the rotor per unit of time, and is generally defined by the equation V (m/sec) =π·D·n, where V is the tip speed, D is the diameter of the rotor, in meters, and n is the rotational speed of the rotor, in revolutions per second. Tip speed is thus a function of the rotor diameter and the rotation rate. Also, tip speed may be calculated by multiplying the circumferential distance transcribed by the rotor tip, 2πR, where R is the radius of the rotor (meters, for example) times the frequency of revolution (for example revolutions (meters, for example) times the frequency of revolution (for example revolutions per minute, rpm).

For colloid mills, typical tip speeds are in excess of 23 m/sec (4500 ft/min) and can exceed 40 m/sec (7900 ft/min). For the purpose of the present disclosure the term 'high shear' refers to mechanical rotor-stator devices, such as mills or mixers, that are capable of tip speeds in excess of 5 m/sec (1000 ft/min) and require an external mechanically driven power device to drive energy into the stream of products to be reacted. A high shear device combines high tip speeds with a very small shear gap to produce significant friction on the material being processed. Accordingly, a local pressure in the range of about 1000 MPa (about 145,000 psi) to about 1050 MPa (152,300 psi) and elevated temperatures at the tip of the shear mixer are produced during operation. In certain embodiments, the local pressure is at least about 1034 MPa (about 150,000 psi).

Figure 2:
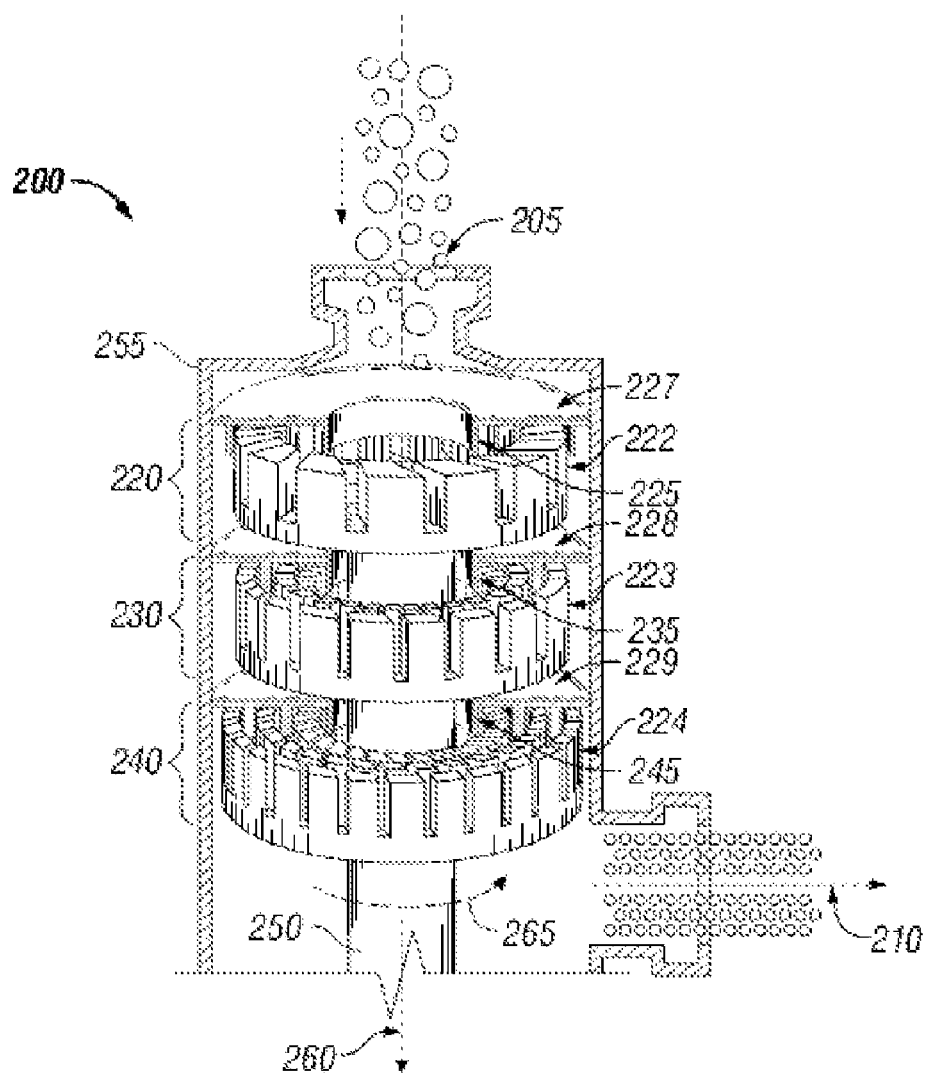
FIG. 2 is a longitudinal cross-section view of a multi-stage high shear device, as employed in an embodiment of the system of FIG. 1.

Referring now to FIG. 2, there is presented a schematic diagram of a high shear device 200. High shear device 200 comprises at least one rotor-stator combination. The rotor-stator combinations may also be known as generators 220, 230, 240 or stages without limitation. The high shear device 200 comprises at least two generators, and most preferably, the high shear device comprises at least three generators.

The first generator 220 comprises rotor 222 and stator 227. The second generator 230 comprises rotor 223, and stator 228; the third generator comprises rotor 224 and stator 229. For each generator 220, 230, 240 the rotor is rotatably driven by input 250. The generators 220, 230, 240 rotate about axis 260 in rotational direction 265. Stator 227 is fixably coupled to the high shear device wall 255.

The generators include gaps between the rotor and the stator. The first generator 220 comprises a first gap 225; the second generator 230 comprises a second gap 235; and the third generator 240 comprises a third gap 245. The gaps 225, 235, 245 are between about 0.025 mm (0.01 in) and 10.0 mm (0.4 in) wide. Alternatively, the process comprises utilization of a high shear device 200 wherein the gaps 225, 235, 245 are between about 0.5 mm (0.02 in) and about 2.5 mm (0.1 in). In certain instances the gap is maintained at about 1.5 mm (0.06 in). Alternatively, the gaps 225, 235, 245 are different between generators 220, 230, 240. In certain instances, the gap 225 for the first generator 220 is greater than about the gap 235 for the second generator 230, which is greater than about the gap 245 for the third generator 240.

Additionally, the width of the gaps 225, 235, 245 may comprise a coarse, medium, fine, and super-fine characterization. Rotors 222, 223, and 224 and stators 227, 228, and 229 may be toothed designs. Each generator may comprise two or more sets of rotor-stator teeth, as known in the art. Rotors 222, 223, and 224 may comprise a number of rotor teeth circumferentially spaced about the circumference of each rotor. Stators 227, 228, and 229 may comprise a number of stator teeth circumferentially spaced about the circumference of each stator. The rotor and the stator may be of any suitable size. In one embodiment, the inner diameter of the rotor is about 64 mm and the outer diameter of the stator is about 60 mm. In further embodiments, the rotor and stator may have alternate diameters in order to alter the tip speed and shear pressures. In certain embodiments, each of three stages is operated with a super-fine generator, comprising a gap of between about 0.025 mm and about 3 mm. When a feed stream 205 including solid particles is to be sent through high shear device 200, the appropriate gap width is first selected for an appropriate reduction in particle size and increase in particle surface area. In embodiments, this is beneficial for increasing catalyst surface area by shearing and dispersing the particles.

High shear device 200 is fed a reaction mixture comprising the feed stream 205. Feed stream 205 comprises an emulsion of the dispersible phase and the continuous phase. Emulsion refers to a liquefied mixture that contains two distinguishable substances (or phases) that will not readily mix and dissolve together. Most emulsions have a continuous phase (or matrix), which holds therein discontinuous droplets, bubbles, and/or particles of the other phase or substance. Emulsions may be highly viscous, such as slurries or pastes, or may be foams, with tiny gas bubbles suspended in a liquid. As used herein, the term "emulsion" encompasses continuous phases comprising gas bubbles, continuous phases comprising particles (e.g., solid catalyst), continuous phases comprising droplets of a fluid that is substantially insoluble in the continuous phase, and combinations thereof.

Feed stream 205 may include a particulate solid catalyst component. Feed stream 205 is pumped through the generators 220, 230, 240, such that product dispersion 210 is formed. In each generator, the rotors 222, 223, 224 rotate at high speed relative to the fixed stators 227, 228, 229. The rotation of the rotors pumps fluid, such as the feed stream 205, between the outer surface of the rotor 222 and the inner surface of the stator 227 creating a localized high shear condition. The gaps 225, 235, 245 generate high shear forces that process the feed stream 205. The high shear forces between the rotor and stator functions to process the feed stream 205 to create the product dispersion 210. Each generator 220, 230, 240 of the high shear device 200 has interchangeable rotor-stator combinations for producing a narrow distribution of the desired bubble size, if feedstream 205 comprises a gas, or globule size, if feedstream 205 comprises a liquid, in the product dispersion 210.

The product dispersion 210 of gas particles, or bubbles, in a liquid comprises an emulsion. In embodiments, the product dispersion 210 may comprise a dispersion of a previously immiscible or insoluble gas, liquid or solid into the continuous phase. The product dispersion 210 has an average gas particle, or bubble, size less than about 1.5 µm; preferably the bubbles are sub-micron in diameter. In certain instances, the average bubble size is in the range from about 1.0 µm to about 0.1 µm. Alternatively, the average bubble size is less than about 400 nm (0.4 µm) and most preferably less than about 100 nm (0.1 µm).

The high shear device 200 produces a gas emulsion capable of remaining dispersed at atmospheric pressure for at least about 15 minutes. For the purpose of this disclosure, an emulsion of gas particles, or bubbles, in the dispersed phase in product dispersion 210 that are less than 1.5 µm in diameter may comprise a micro-foam. Not to be limited by a specific theory, it is known in emulsion chemistry that sub-micron particles, or bubbles, dispersed in a liquid undergo movement primarily through Brownian motion effects. The bubbles in the emulsion of product dispersion 210 created by the high shear device 200 may have greater mobility through boundary layers of solid catalyst particles, thereby facilitating and accelerating the catalytic reaction through enhanced transport of reactants.

The rotor is set to rotate at a speed commensurate with the diameter of the rotor and the desired tip speed as described hereinabove. Transport resistance is reduced by incorporation of high shear device 200 such that the velocity of the reaction is increased by at least about 5%. Alternatively, the high shear device 200 comprises a high shear colloid mill that serves as an accelerated rate reactor (ARR). The accelerated rate reactor comprises a single stage dispersing chamber. The accelerated rate reactor comprises a multiple stage inline disperser comprising at least 2 stages.

Selection of the high shear device 200 is dependent on throughput requirements and desired particle or bubble size in the outlet dispersion 210. In certain instances, high shear device 200 comprises a Dispax Reactor® of IKA® Works, Inc. Wilmington, N.C. and APV North America, Inc. Wilmington, Mass. Model DR 2000/4, for example, comprises a belt drive, 4M generator, PTFE sealing ring, inlet flange 1" sanitary clamp, outlet flange ¾" sanitary clamp, 2 HP power, output speed of 7900 rpm, flow capacity (water) approximately 300 l/h to approximately 700 l/h (depending on generator), a tip speed of from 9.4 m/s to about 41 m/s (about 1850 ft/min to about 8070 ft/min). Several alternative models are available having various inlet/outlet connections, horsepower, nominal tip speeds, output rpm, and nominal flow rate.

Without wishing to be limited to a particular theory, it is believed that the level or degree of high shear mixing is sufficient to increase rates of mass transfer and may also produce localized non-ideal conditions that enable reactions to occur that would not otherwise be expected to occur based on Gibbs free energy predictions. Localized non ideal conditions are believed to occur within the high shear device resulting in increased temperatures and pressures with the most significant increase believed to be in localized pressures. The increase in pressures and temperatures within the high shear device are instantaneous and localized and quickly revert back to bulk or average system conditions once exiting the high shear device. In some cases, the high shear device induces cavitation of sufficient intensity to dissociate one or more of the reactants into free radicals, which may intensify a chemical reaction or allow a reaction to take place at less stringent conditions than might otherwise be required. Cavitation may also increase rates of transport processes by producing local turbulence and liquid micro-circulation (acoustic streaming).

Vessel. Vessel or reactor 110 is any type of vessel in which a multiphase reaction can be propagated to carry out the above-described conversion reaction(s). For instance, a continuous or semi-continuous stirred tank reactor, or one or more batch reactors may be employed in series or in parallel. In some applications vessel 110 may be a tower reactor, and in others a tubular reactor or multi-tubular reactor. A catalyst inlet line 115 may be connected to vessel 110 for receiving a catalyst solution or slurry during operation of the system.

Vessel 110 may include one or more of the following components: stirring system, heating and/or cooling capabilities, pressure measurement instrumentation, temperature measurement instrumentation, one or more injection points, and level regulator (not shown), as are known in the art of reaction vessel design. For example, a stirring system may include a motor driven mixer. A heating and/or cooling apparatus may comprise, for example, a heat exchanger. Alternatively, as much of the conversion reaction may occur within HSD 140 in some embodiments, vessel 110 may serve primarily as a storage vessel in some cases. Although generally less desired, in some applications vessel 110 may be omitted, particularly if multiple high shear devices/reactors are employed in series, as further described below.

Heat Transfer Devices. In addition to the above-mentioned heating/cooling capabilities of vessel 110, other external or internal heat transfer devices for heating or cooling a process stream are also contemplated in variations of the embodiments illustrated in FIG. 1. Some suitable locations for one or more such heat transfer devices are between pump 105 and HSD 140, between HSD 140 and vessel 110, and between vessel 110 and pump 105 when system 1 is operated in multipass mode. Some non-limiting examples of such heat transfer devices are shell, tube, plate, and coil heat exchangers, as are known in the art.

Pumps. Pump 105 is configured for either continuous or semi-continuous operation, and may be any suitable pumping device that is capable of providing greater than 2 atm pressure, preferably greater than 3 atm pressure, to allow controlled flow through HSD 140 and system 1. For example, a Roper Type 1 gear pump, Roper Pump Company (Commerce Georgia) Dayton Pressure Booster Pump Model 2P372E, Dayton Electric Co (Niles, Ill.) is one suitable pump. Preferably, all contact parts of the pump comprise stainless steel. In some embodiments of the system, pump 105 is capable of pressures greater than about 20 atm. In addition to pump 105, one or more additional, high pressure pump (not shown) may be included in the system illustrated in FIG. 1. For example, a booster pump, which may be similar to pump 105, may be included between HSD 140 and vessel 110 for boosting the pressure into vessel 110. As another example, a supplemental feed pump, which may be similar to pump 105, may be included for introducing additional reactants or catalyst into vessel 110.

Hydrogenation of Aldehydes and Ketones. In operation for the catalytic hydrogenation of aldehydes and/or ketones, respectively, a dispersible hydrogen-containing gas stream is introduced into system 100 via line 122, and combined in line 113 with either an aldehyde and/or ketone stream to form a gas-liquid stream. The hydrogen-containing gas may be hydrogen, or any other suitable molecular hydrogen-containing gas, or mixture of gases, for example. Alternatively, the hydrogen-containing gas may be fed directly into HSD 140, instead of being combined with the liquid reactant (i.e., aldehyde and/ketone) in line 113. Pump 105 is operated to pump the liquid reactant (aldehyde and/or ketone) through line 121, and to build pressure and feed HSD 140, providing a controlled flow throughout high shear device (HSD) 140 and high shear system 100.

In a preferred embodiment, hydrogen gas may continuously be fed into the aldehyde/ketone stream 112 to form a high shear device feed stream (e.g. a gas-liquid stream) in line 113. In high shear device 140, hydrogen gas and the aldehyde and/or ketone are highly dispersed such that nanobubbles and/or microbubbles of the hydrogen-containing gas are formed for superior dissolution of the hydrogen-containing gas into solution. Once dispersed, the dispersion may exit high shear device 140 at high shear device outlet line 118. Stream 118 may optionally enter fluidized or fixed bed 142 in lieu of a slurry catalyst process. However, in a slurry catalyst embodiment, high shear outlet stream 118 may directly enter hydrogenation reactor 110 for hydrogenation. The reaction stream may be maintained at the specified reaction temperature, using cooling coils in the reactor 110 to maintain reaction temperature. Hydrogenation products (e.g. alcohols) may be withdrawn at product stream 116.

In an exemplary embodiment, the high shear device comprises a commercial disperser such as IKA® model DR 2000/4, a high shear, three stage dispersing device configured with three rotors in combination with stators, aligned in series. The disperser is used to create the dispersion of hydrogen-containing gas in the liquid medium comprising an aldehyde and/or ketone (i.e., "the reactants"). The rotor/stator sets may be configured as illustrated in FIG. 2, for example. The combined reactants enter the high shear device via line 113 and enter a first stage rotor/stator combination having circumferentially spaced first stage shear openings. The coarse dispersion exiting the first stage enters the second rotor/stator stage, which has second stage shear openings. The reduced bubble-size dispersion emerging from the second stage enters the third stage rotor/stator combination having third stage shear openings. The dispersion exits the high shear device via line 118. In some embodiments, the shear rate increases stepwise longitudinally along the direction of the flow. For example, in some embodiments, the shear rate in the first rotor/stator stage is greater than the shear rate in subsequent stage(s). In other embodiments, the shear rate is substantially constant along the direction of the flow, with the stage or stages being the same. If the high shear device includes a PTFE seal, for example, the seal may be cooled using any suitable technique that is known in the art. For example, the reactant stream flowing in line 113 may be used to cool the seal and in so doing be preheated as desired prior to entering the high shear device.

The rotor of HSD 140 is set to rotate at a speed commensurate with the diameter of the rotor and the desired tip speed. As described above, the high shear device (e.g., colloid mill) has either a fixed clearance between the stator and rotor or has adjustable clearance. HSD 140 serves to intimately mix the hydrogen-containing gas and the reactant liquid (i.e., aldehyde and/or ketone). In some embodiments of the process, the transport resistance of the reactants is reduced by operation of the high shear device such that the velocity of the reaction is increased by greater than a factor of about 5. In some embodiments, the velocity of the reaction is increased by at least a factor of 10. In some embodiments, the velocity is increased by a factor in the range of about 10 to about 100 fold. In some embodiments, HSD 140 delivers at least 300 L/h with a power consumption of 1.5 kW at a nominal tip speed of at least 4500 ft/min, and which may exceed 7900 ft/min (140 m/sec).

Although measurement of instantaneous temperature and pressure at the tip of a rotating shear unit or revolving element in HSD 140 is difficult, it is estimated that the localized temperature seen by the intimately mixed reactants may be in excess of 500° C. and at pressures in excess of 500 kg/cm$^2$ under high shear conditions. The high shear mixing results in dispersion of the hydrogen-containing gas in micron or submicron-sized bubbles. In some embodiments, the resultant dispersion has an average bubble size less than about 1.5 µm. Accordingly, the dispersion exiting HSD 140 via line 118 comprises micron and/or submicron-sized gas bubbles. In some embodiments, the mean bubble size is in the range of about 0.4 µm to about 1.5 µm. In some embodiments, the mean bubble size is less than about 400 nm, and may be about 100 nm in some cases. In many embodiments, the microbubble dispersion is able to remain dispersed at atmospheric pressure for at least 15 minutes.

Once dispersed, the resulting gas/aldehyde, gas/ketone, or gas/ketone/aldehyde dispersion exits HSD 140 via line 118 and feeds into vessel 110, as illustrated in FIG. 1. As a result of the intimate mixing of the reactants prior to entering vessel 110, a significant portion of the chemical reaction may take place in HSD 140, with or without the presence of a catalyst. Hydrogenation may also occur in the HSD resulting in alcohol output from the HSD. This may be driven by the reaction conditions within the HSD. Accordingly, in some embodiments, reactor/vessel 110 may be used primarily for heating and separation of volatile reaction products from the alcohol product. Alternatively, or additionally, vessel 110 may serve as a primary reaction vessel where most of the alcohol product is produced. Vessel/reactor 110 may be operated in either continuous or semi-continuous flow mode, or it may be operated in batch mode. The contents of vessel 110 may be maintained at a specified reaction temperature using heating and/or cooling capabilities (e.g., cooling coils) and temperature measurement instrumentation. Pressure in the vessel may be monitored using suitable pressure measurement instrumentation, and the level of reactants in the vessel may be controlled using a level regulator (not shown), employing techniques that are known to those of skill in the art. The contents are stirred continuously or semi-continuously.

Commonly known hydrogenation reaction conditions may suitably be employed as the conditions of the production of an alcohol by hydrogenating the aldehyde and/or the ketone by using the catalysts. There is no particular restriction as to the reaction conditions. However, the hydrogen pressure is selected usually within a range of from about atmospheric pressure to 100 atm, more preferably from 10 to 60 atm, and the reaction temperature may be within a range of from about 15° C. to about 350° C., alternatively from about 20° C. to about 220° C.

The hydrogen-containing feed gas supplied to system 100 preferably contains a major amount of hydrogen and at most a minor amount of one or more inert gases, such as nitrogen, methane, other low molecular weight hydrocarbons, such as ethane, propane, n-butane and iso-butane, carbon oxides, neon, argon or the like. The hydrogen-containing gas may include at least about 50 mole % up to about 95 mole % or more (e.g. about 99 mole %) of $H_2$ with the balance comprising one or more of $N_2$, CO, $CO_2$, Ar, Ne, $CH_4$ and other low molecular weight saturated hydrocarbons. In some cases, e.g. when using nickel catalysts, the presence of CO and $CO_2$ cannot be tolerated and the total carbon oxides concentration in the hydrogen-containing feed gas should not be more than about 5 ppm. Such hydrogen-containing gases can be obtained in conventional manner from synthesis gas and other usual sources of hydrogen-containing gases, followed by appropriate pre-treatment to remove impurities, such as sulphurous impurities (e.g. $H_2S$, COS, $CH_3SH$, $CH_3SCH_3$, and $CH_3SSCH_3$) and halogen-containing impurities (e.g. HCl and $CH_3Cl$) which would exert a deleterious influence on catalytic activity, i.e. catalyst inhibition, poisoning or deactivation. Suitable hydrogen-containing gases may be prepared according to usual production techniques. Thus the hydrogen-containing feed gas may be, for example, a 94 mole % hydrogen stream produced by steam reforming of natural gas.

The aldehyde and/or the ketone for the reaction may be used alone or in combination as a mixture of different types. The aldehydes and ketones to be hydrogenated can have any structure, such as, aliphatic, aromatic, heteroaromatic, aliphatic-aromatic or aliphatic-heteroaromatic. They can also contain other functional groups, and it should be determined beforehand whether these functional groups should remain unchanged or should be hydrogenated themselves.

Embodiments of the disclosed process may be suitable for hydrogenating straight or branched aldehyde(s). The described process may be used for hydrogenating a wide variety of straight or branched chain, saturated or unsaturated aldehydes containing from 2 to 22 carbon atoms. These aldehydes include without limitation, saturated aldehydes like acetaldehyde, propionaldehyde, isobutyraldehyde, n-butyraldehyde, isopentylaldehyde, n-pentyl aldehyde, 2-methyl pentyl aldehyde, crotonaldehyde, 2-ethyl hexaldehyde, methyl pentyl aldehyde, 2-ethyl butyraldehyde, and unsaturated C3-8 aldehydes like acrolein, 2-ethyl propylacrolein, and benzaldehyde, furaldehyde, pyridinylaldehyde and the like. The aldehyde may be in a substantially pure state or admixed with a component(s) other than an aldehyde. Further, a mixture of aldehydes may be employed. It is contemplated that an alcohol, an ester for an aliphatic hydrocarbon, may be used as a solvent.

The ketone may be any compound having the formula, $R_1(C=O)R_2$. $R_1$-$R_2$ may independently comprise an alkyl group, a cyclic group, an aromatic group, a heterocyclic group, an alkenyl group, or combinations thereof. $R_1$-$R_2$ may be the same or different from one another.

Catalyst. If a catalyst is used to promote the hydrogenation reaction, it may be introduced into the vessel via line 115, as an aqueous or nonaqueous slurry or stream. Alternatively, or additionally, catalyst may be added elsewhere in the system 100. For example, catalyst slurry may be injected into line 121. In some embodiments, line 121 may contain a flowing aldehyde and/or ketone stream and/or aldehyde/ketone recycle stream from vessel 110.

In embodiments, any catalyst suitable for catalyzing a hydrogenation reaction may be employed. An inert gas such as nitrogen may be used to fill reactor 110 and purge it of any air and/or oxygen. Any catalyst known to those of skill in the art may also be utilized for hydrogenation. Suitable catalysts may be any of the catalysts normally used for hydrogenation of aldehydes and/or ketones. Catalysts such as these generally comprise one or more transition metals or compounds of one or more transition metals in a form suitable for hydrogenation. Catalysts comprising one or more metals from group VIII or VIIIA of the periodic system of elements and/or one or more of their compounds are preferably used for the process according to the invention. The metals iron, ruthenium, osmium, cobalt, rhodium, iridium, nickel, palladium and platinum and compounds thereof have proved to be particularly successful. For economic reasons, and also by virtue of its particular efficiency, nickel or one or more of its compounds is particularly conveniently used as catalyst for the hydrogenation of aldehydes and/or ketones in the disclosed process. These include copper based and platinum based hydrogenation catalysts. Other examples of suitable catalysts include without limitation, copper chromite; cobalt compounds; nickel; nickel compounds which may contain small amounts of chromium or other promoters; mixtures of copper and nickel and/or chromium; and a mixture of reduced copper oxide-zinc oxide. Embodiments of the process may employ any of the described catalysts.

In an embodiment, the catalyst may be a ruthenium catalyst. The ruthenium catalyst of the present invention can be obtained by reducing the alkali metal ruthenate with a reducing agent selected from the group consisting of methanol, formaldehyde and formic acid. It is preferably supported on a carrier. There is no particular restriction as to the carrier to be used. It may be active carbon, alumina or silica. However, it is preferred to use active carbon as the carrier, particularly for the production of a highly active catalyst. For the preparation of a carrier-supported catalyst, an aqueous solution or an aqueous alkaline solution of an alkali metal ruthenate is first impregnated within a carrier.

Embodiments may utilize catalysts in which the catalytically active metallic ruthenium is precipitated in finely divided form onto suitable carrier materials such as aluminum oxide, titanium dioxide, kieselguhr, silica gel, molecular sieves, and zeolites of natural or synthetic origin. Catalysts whose carrier material consists of activated carbon are preferred. According to the invention, these carrier catalysts are employed as finely divided powders as before, but in compacted lumpy form. Catalyst may be fed into reactor 110 through catalyst feed stream 115.

The bulk or global operating temperature of the reactants is desirably maintained below their flash points. In some embodiments, the operating conditions of system 100 comprise a temperature in the range of from about 50° C. to about 300° C. In specific embodiments, the reaction temperature in vessel 110, in particular, is in the range of from about 90° C. to about 220° C. In some embodiments, the reaction pressure in vessel 110 is in the range of from about 5 atm to about 50 atm.

The dispersion may be further processed prior to entering vessel 110 (as indicated by arrow 18), if desired. In vessel 110, aldehyde and/or ketone hydrogenation occurs via catalytic hydrogenation. The contents of the vessel are stirred continuously or semi-continuously, the temperature of the reactants is controlled (e.g., using a heat exchanger), and the fluid level inside vessel 110 is regulated using standard techniques. Aldehyde and/or ketone hydrogenation may occur either continuously, semi-continuously or batch wise, as desired for a particular application. Any reaction gas that is produced exits reactor 110 via gas line 117. This gas stream may comprise unreacted aldehydes and/or ketones, and hydrogen-containing gas, for example. Preferably the reactants are selected so that the gas stream comprises less than about 6% hydrogen-containing gas by weight. In some embodiments, the reaction gas stream in line 117 comprises from about 1% to about 4% hydrogen-containing gas by weight. The reaction gas removed via line 117 may be further treated, and the components may be recycled, as desired.

The reaction product stream including unconverted aldehydes and/or ketones and corresponding byproducts exits vessel 110 by way of line 116. The alcohol product may be recovered and treated as known to those of skill in the art.

Multiple Pass Operation. In the embodiment shown in FIG. 1, the system is configured for single pass operation, wherein the output from vessel 110 goes directly to further processing for recovery of alcohol product. In some embodiments it may be desirable to pass the contents of vessel 110, or a liquid fraction containing unreacted aldehyde and/or ketone, through HSD 140 during a second pass. In this case, line 116 is connected to line 121 via dotted line 120, and the recycle stream from vessel 110 is pumped by pump 105 into line 113 and thence into HSD 140. Additional hydrogen-containing gas may be injected via line 122 into line 113, or it may be added directly into the high shear device (not shown).

Multiple High shear devices. In some embodiments, two or more high shear devices like HSD 140, or configured differently, are aligned in series, and are used to further enhance the reaction. Their operation may be in either batch or continuous mode. In some instances in which a single pass or "once through" process is desired, the use of multiple high shear devices in series may also be advantageous. In some embodiments where multiple high shear devices are operated in series, vessel 110 may be omitted. In some embodiments, multiple high shear devices 140 are operated in parallel, and the outlet dispersions therefrom are introduced into one or more vessel 110.

While embodiments of the invention have been shown and described, modifications thereof can be made by one skilled in the art without departing from the spirit and teachings of the invention. The embodiments described herein are exemplary only, and are not intended to be limiting. Many variations and modifications of the invention disclosed herein are possible and are within the scope of the invention. Where numerical ranges or limitations are expressly stated, such express ranges or limitations should be understood to include iterative ranges or limitations of like magnitude falling within the expressly stated ranges or limitations. Use of broader terms such as comprises, includes, having, etc. should be understood to provide support for narrower terms such as consisting of, consisting essentially of, comprised substantially of, and the like. Accordingly, the scope of protection is not limited by the description set out above but is only limited by the claims which follow, that scope including all equivalents of the subject matter of the claims. Each and every original claim is incorporated into the specification as an embodiment of the invention. Thus, the claims are a further description and are an addition to the preferred embodiments of the present invention. The disclosures of all patents, patent applications, and publications cited herein are hereby incorporated by reference, to the extent they provide exemplary, procedural or other details supplementary to those set forth herein.

What is claimed is:

1. A method of hydrogenating an aldehyde or a ketone comprising:
   a) introducing a gas stream comprising hydrogen into a high shear device;
   b) introducing a liquid stream comprising an aldehyde or ketone into said high shear device;
   c) forming a dispersion in said high shear device comprising gas bubbles having a mean diameter of less than about 1 micron; and
   d) contacting the dispersion with a catalyst in a reactor to hydrogenate the aldehyde or the ketone.

2. The method of claim 1, wherein the gas bubbles have an average diameter of less than about 400 nm.

3. The method of claim 1, wherein the gas bubbles have an average diameter of no more than about 100 nm.

4. The method of claim 1, wherein the liquid stream includes a liquid-gas stream formed by mixing an aldehyde- or ketone-containing stream with a second hydrogen-containing gas stream.

5. The method of claim 1, wherein (c) comprises subjecting said gas and liquid to high shear mixing at a tip speed of at least about 23 m/sec.

6. The method of claim 5, wherein said high shear mixing produces a local pressure of at least about 1000 MPa at said tip.

7. The method of claim 1, wherein (c) comprises subjecting said gas and liquid to a shear rate of greater than about 20,000 s$^{-1}$.

8. The method of claim 1, wherein forming said dispersion comprises an energy expenditure of at least about 1000 W/m$^3$.

9. The method of claim 1, wherein said high shear device increases the reaction rate of said hydrogenation by at least 5 times.

10. The method of claim 1 further comprising contacting the dispersion with a hydrogenation catalyst to form an alcohol.

11. The method of claim 1, wherein said reactor is a fixed bed reactor comprising the catalyst.

12. The method of claim 1, wherein the catalyst is selected from the group consisting of copper, zinc, iron, ruthenium, osmium, cobalt, rhodium, iridium, nickel, palladium, platinum, and combinations thereof.

13. The method of claim 1 comprising mixing the catalyst with the liquid stream to form a slurry before (b).

14. The method of claim 1, wherein (d) results in the production of an alcohol.

15. The method of claim 1, wherein said high shear device comprises a rotor and a stator separated by a shear gap in the range of from about 0.02 mm to about 5 mm, wherein the shear gap is a minimum distance between said rotor and said stator.

16. The method of claim 1, wherein the high shear device comprises two or more rotors and two or more stators.

17. The method of claim 1, wherein said high shear device comprises a rotor tip and said device is configured for operating at a flow rate of at least 300 L/h at a tip speed of at least about 23 m/sec.

18. The method of claim 1 further comprising utilizing at least two high shear devices.

19. The method of claim 1, wherein the high shear device is capable of producing a dispersion of hydrogen gas bubbles having a mean diameter of less than about 5 μm in the liquid.

20. The method of claim 1, wherein the high shear device comprises a high shear mill having a tip speed of greater than about 5 m/s (1000 ft/min).

* * * * *